April 30, 1946. H. R. BOHANNON Plant Pat. 685
GERANIUM PLANT
Filed July 12, 1945
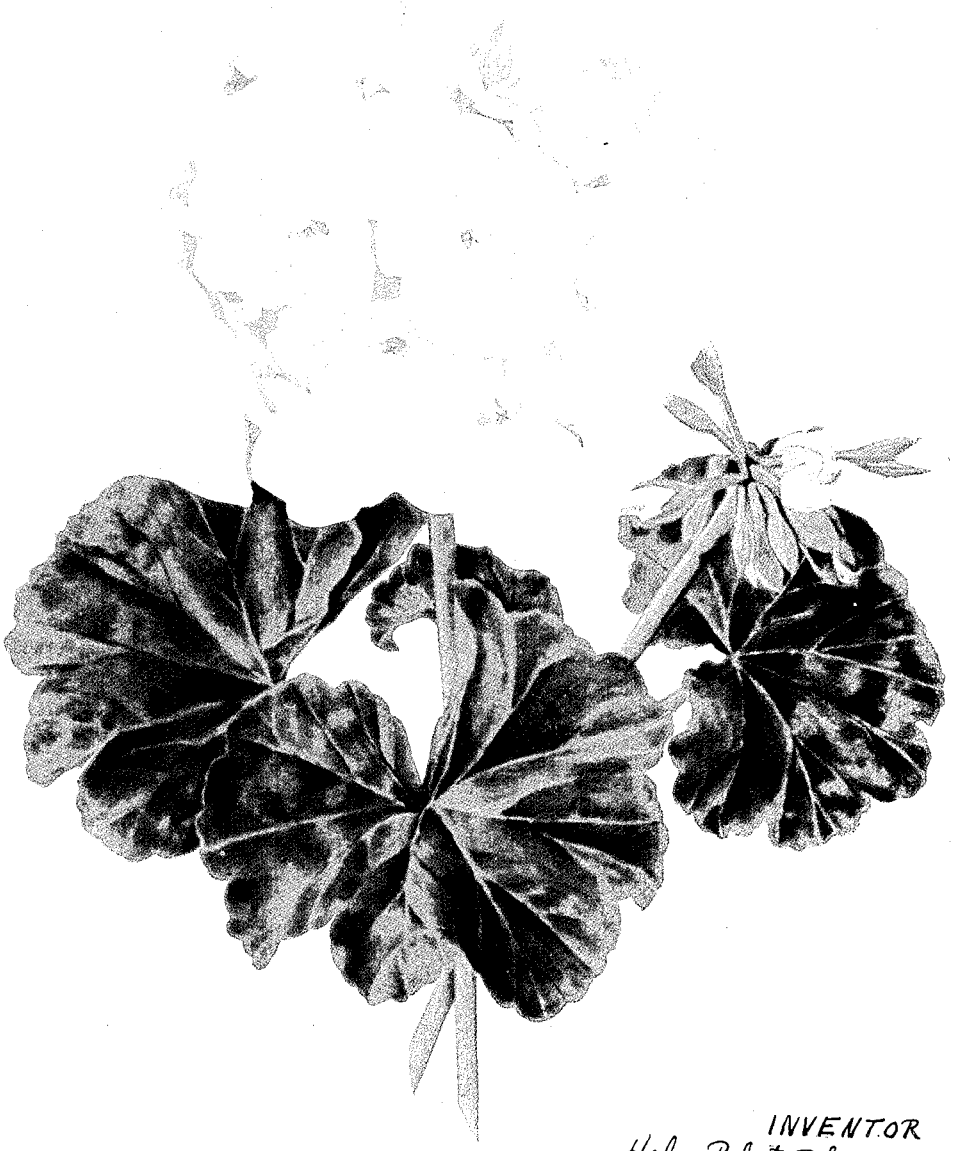
INVENTOR
Helen Roberts Bohannon
By Orville M. Kile
Plant Pat. Agt.

Patented Apr. 30, 1946

Plant Pat. 685

UNITED STATES PATENT OFFICE

685

GERANIUM PLANT

Helen Roberts Bohannon, Berkeley, Calif., assignor to Paul J. Howard Company, and Paul J. Howard's California Flowerland, Los Angeles, Calif., a corporation of California Application July 12, 1945, Serial No. 604,572

1 Claim. (Cl. 47—60)

My present invention relates to a new and improved variety of geranium plant and is the result of definite breeding efforts carried on by me in connection with attempts to produce varieties of the general type of Nouvelle Aurore but with a hardier constitution. I crossed Nouvelle Aurore with an unnamed seedling, then took one of the first year crosses and back-crossed it with Nouvelle Aurore. The present variety is the result of one of these back crosses and is one of a series of desirable varieties.

This new variety is a continuous and very prolific bloomer and the florets are very large and of "pansy form" with color of pleasing pastel. Accompanying illustrations show a truss of florets, together with buds and foliage of this new variety, in the original approximately their true size and colors.

Following is a description of the flower and plant of this new variety of geranium. Color plates refer to the Horticultural Colour Chart except where otherwise indicated.

*The plant*

Growth: Vigorous and compact. Attains an average height of 12 to 18 inches when grown as a pot plant, and 2 feet when grown outdoors in this climate.

Blooming habit: Very free and continuous bloomer both outdoors and as a pot plant. A plant produced in a 4-inch pot produces 2 or 3 trusses at one time, while a full grown plant produces 40 to 50 trusses at one time.

Inflorescence: Enormous, globular, compact umbel or truss measuring 5½ to 6 inches in diameter.

Foliage:

*Quantity.*—Abundant.

*Size.*—Average to large in size, approximately 3½ to 4 inches in diameter.

*Color.*—Spinach Green (Pl. V, Ridgway's).

*Shape.*—Disk-shaped and undulate with deeply lobulated edges.

*Texture.*—Firm; thick; upper surface smooth, lower surface moderately hairy.

Stem: Long and strong.

Peduncle: Strong, slightly hairy. Color same as foliage.

*The flower*

Truss:

*Size.*—Enormous, measuring up to 6 inches in diameter.

*Shape.*—Compact and almost truly globular.

*Number of florets.*—Average to a truss is 20 to 25.

*Lasting quality.*—Remains in bloom 10 days to 2 weeks.

Bud:

*Sepals.*—Long and pointed.

*Color.*—Mandarin Red (17).

*Form.*—Pointed.

Florets:

*Size.*—Approximately two inches in diameter.

*Petalage.*—Single, with 5 petals.

*Color.*—Azalea Pink (618) tinged at edges with Mandarin Red (17/1), lightening toward center and merging into a large white eye in center of floret. Center markings are Carmine (21) to (21/2). Color does not fade until floret dies.

*Texture and aspect.*—Firm and glistening.

*Form.*—Petals are smooth edged and overlapping in pansy-like effect. When all florets are open the globular truss is from 5½ to 6 inches in diameter when grown under favorable conditions.

*Lasting quality.*—Average floret lasts 2 to 3 days and the truss remains in bloom for 10 days to 2 weeks.

*Behavior.*—Petals drop cleanly, do not die on stem.

Having thus disclosed my invention, I claim:

The new and useful variety of geranium plant, substantially as shown and described, characterized particularly by its healthy growth; its continuous and exceptionally free blooming habit; its exceedingly large compact globular truss; its large pansy-like florets with overlapping petals, and the distinctive color of its flowers ranging from Azalea Pink to Mandarin Red except for the white eye.

HELEN ROBERTS BOHANNON.